United States Patent [19]

Paulin

[11] 4,309,782
[45] Jan. 12, 1982

[54] DEVICE FOR COLLECTING FECAL SPECIMENS

[76] Inventor: Esteban Paulin, 5 Guerrero, Queretaro, Mexico

[21] Appl. No.: 186,348

[22] Filed: Sep. 11, 1980

[51] Int. Cl.³ .................... A47K 17/00; E03D 13/00
[52] U.S. Cl. ...................................... 4/661; 4/144.1; 4/144.2; 4/301
[58] Field of Search ............ 4/661, 144.1, 301, 144.2, 4/144.3, 144.4; 128/349 R, 2 F, 275, 295, 349, 767

[56] References Cited

U.S. PATENT DOCUMENTS

| | | | |
|---|---|---|---|
| 2,801,424 | 8/1957 | Mercer | 4/661 |
| 2,840,826 | 7/1958 | Ebbesen et al. | 4/661 |
| 3,571,817 | 3/1972 | Gosnell | 4/144.1 |
| 3,588,921 | 6/1971 | Nagel | 4/661 |
| 3,625,654 | 12/1971 | Duyne | 4/661 |
| 3,654,638 | 4/1972 | Nye | 4/144.1 |
| 3,754,287 | 8/1973 | Taylor | 4/661 |
| 3,775,777 | 12/1973 | Roberts, Jr. | 4/661 |
| 4,203,169 | 5/1980 | Dale | 4/144.1 |

*Primary Examiner*—Henry K. Artis
*Attorney, Agent, or Firm*—Fleit & Jacobson

[57] ABSTRACT

A relatively inexpensive, simple and practical device for interposition between the seat of a toilet stool bowl and the upper edge of the bowl, for collecting, when in position, the fecal discharge of a patient whose feces is to be examined; the device normally being folded and stored in a sterile mailer together with a wooden spatula; the specimen collecter being produced from biodegradable materials, and including a foldable base plate which has a forward margin spaced from the forward portion of the toilet bowl to permit ready discharge of urine without contaminating or diluting the fecal sample, and the base element, when disposed in an unfolded or flat condition, having a rear tab clamped beneath the stool seat and disposing a bag-like element, adhesively secured to the base plate in an optimum position to receive the fecal specimen; the bag-like element being produced from a disposable paper-product material similar to that from which disposable diapers are produced; the bag-like element having a transverse open back permitting the spatula to be used to scrape-out excess of the specimen into the toilet bowl; the bag-like element having a rounded lower configuration causing the specimen to accumulate therein when the device is in use.

11 Claims, 4 Drawing Figures

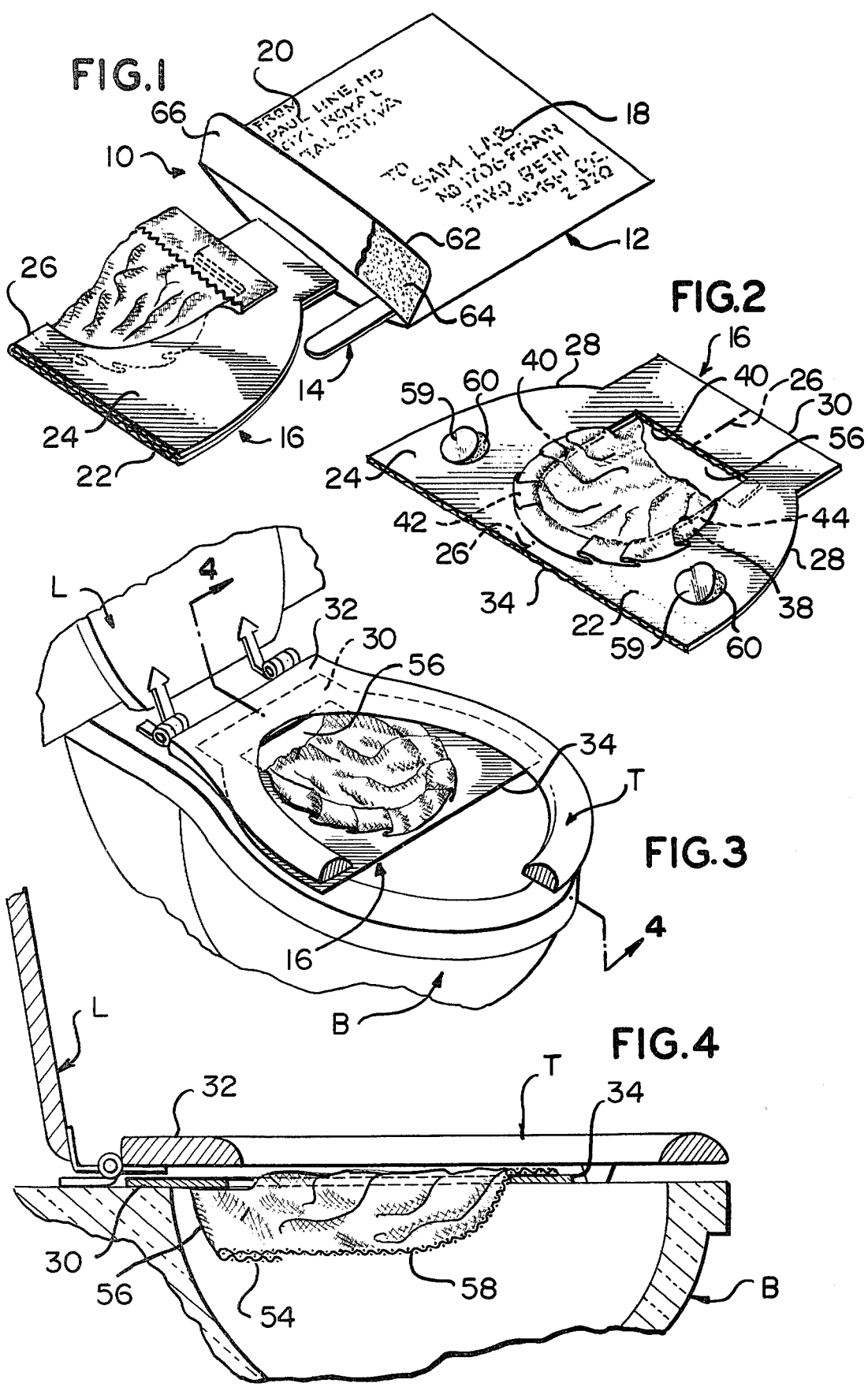

DEVICE FOR COLLECTING FECAL SPECIMENS

BACKGROUND OF THE INVENTION

The field of invention generally concerns stool specimen collection kits and, more particularly, to a device adapted to be positioned over the bowl of a toilet in an optimum position relative to a users rectum for collecting substantially the entire fecal discharge, but providing means whereby the sample or specimen is not intermixed or diluted with urine.

Fecal specimen collectors are, per se, not new. For example, the patent to Brockman, U.S. Pat. No. 3,540,433, discloses essentially a strainer device of a relatively permanent character and including particularly conformed screen apertures for retaining a stool specimen; the device being so conformed as to cause urine and feces to be mixed, while the foraminous container permitting urine to drain into the toilet bowl.

The patent to Nagel, U.S. Pat. No. 3,588,921, as in the case of the Brockman patent, is positioned beneath the stool seat, has a relatively complicated folding catching box, but shows a forward opening permitting urine to be passed directly into the toilet bowl without first passing into the feces collector. This is a complicated device and would probably be relatively difficult for uneducated, perhaps third world people to understand.

The patent to Ott, U.S. Pat. No. 3,501,781, shows a device somewhat similar to that of the patent to Brockman and is used to collect the entire fecal sample as well as the urine passed while moving the bowels. Further, the patent to Roberts, Jr., U.S. Pat. No. 3,775,777, shows a foldable device somewhat similar to the device of the patent to Nagel; however, in this case, the entire stool is substantially covered.

Bed pans have incorporated disposable liners and the like, as illustrated, for example, by the patents to Presseisen, U.S. Pat. No. 3,061,840, or Whitney, 3,377,631. Other disposable units used for relief in vehicles, etc., are the patents to Szabo, U.S. Pat. No. 2,654,892, Billeb, 2,315,390, Ersek, 3,346,883, and Rinehart, 3,422,985.

SUMMARY OF THE INVENTION

It is an object of the invention to provide a fecal specimen collection device which is relatively inexpensive to produce, which is readily packaged before and after being used, which is readily used by one having a modest education and comprehension, which is biodegradable and thus ecologically acceptable, and which can be readily used in remote, or in third world countries, where the problems of dysentary and the like require continued medical supervision, including fecal sampling and testing.

Another object of the invention is to provide a device which is of the character mentioned above in which portions of the specimen can be readily scraped into the toilet bowl, the device being so conformed as to substantially eliminate urine mixture and/or dilution of the fecal sample or specimen, the device being readily repackaged with minimum contamination of the specimen and preserving essentially sanitary conditions to minimize the spread of infection which may be contained in the fecal sample being collected.

These, together with other objects and advantages, will become apparent from the following description, when taken with the drawing, forming a part thereof in which:

BRIEF DESCRIPTION OF THE DRAWING

FIG. 1 is a fragmentary perspective view of the fecal sampling kit, including the fecal sample or specimen collector, in a medically folded condition and being either removed or inserted in a mailer and including a disposable spatula for scraping away a portion of the sample prior to mailing to a testing laboratory;

FIG. 2 is a perspective view of the specimen collector, showing one of the pressure-sensitive spots with its protective cover partially removed;

FIG. 3 is a partial perspective view of a toilet stool with the fecal specimen collector installed in its operative position on the toilet bowl; the toilet seat being partially broken away; and FIG. 4 is an enlarged section taken on the plane of line 4—4 of FIG. 3.

DESCRIPTION OF THE INVENTION

Referring first to FIG. 1, a fecal specimen collection kit is indicated generally at 10 and comprises a mailer envelope 12, a spatula 14 (similar to a tongue depressor), and a fecal specimen collector 16 which is in its folded or stored condition.

The mailer envelope will preferably be preaddressed for the testing laboratory, as indicated at 18, and have the return address 20 of the sender or physician. The envelope will have been sterilized in any conventional manner, i.e. using heat, gases, etc., and the sealing flap 22 of the mailer will preferably have a pressure sensitive adhesive to insure ready and complete sealing.

As mentioned above, the scraper or spatula may be produced of wood, paperboard, etc., and will be biodegradable as will be the mailing envelope.

The fecal specimen collector 16 includes two complimentary halves 22 and 24 defined by a medial fold or score line 26 as best seen in FIG. 2. The halves 22, 24 are generally semi-circular at the rear margin as indicated at 28 and generally conforming to the configuration of the rear half of a toilet bowl, and the curved rear margin is integral with a rearwardly projecting tab 30 having a rectangular margin and being positionable beneath a similar portion of the toilet seat 32, as seen in FIGS. 3 and 4. The halves 22, 24 will be oriented into a substantial plane, when unfolded about score line 26, and when so unfolded will be substantially rigid. It will be seen that the arcuate or curved margins 28 terminate at a forward, transverse linear margin 34, which define with the forward portion of the toilet bowl and/or toilet seat a substantially forward opening 36 to permit the ready urination of both male and female without contamination of the fecal specimen being collected. The halves 22, 24 are produced from any suitable biodegradable material such as paperboard, cardboard or the like.

The halves 22, 24 are each provided with cut-out portions 38 and 40, respectively, having marginal definitions similar to, but spaced from, the outer margins of the halves, and defining a through opening in the device as illustrated in FIG. 2, for example. A rear free margin 40, the purpose of which is to be described.

Adhesively secured to both the upper and partially to the lower surface of the halves 22, 24, as indicated at 42 and 44, respectively, and overlying the cut-outs 38 and 40, is a bag-like, specimen catcher 46 which comprises a disposable biodegradable material corresponding to that used for producing disposable diapers. This material is relatively microporous and will be of the character which would permit excessive moisture in a sample to pass through the bag and into the toilet bowl.

More specifically, the bag in this exemplary embodiment is produced by securing a rectangular sheet and forming a plurality of pleats 48, the forward upper surface of the element as seen in FIG. 3; then pleats 50 are progressively formed along the sides and the sheet passes through the cut-out portions 38, 40, where after still further contouring pleats are formed at 52; the rear terminal edge 54 of the bag is overlapped for reinforcement as most clearly seen in FIG. 4; the rear edge 54 is spaced below the unfolded halves 22, 24 and thus form an opening 56 through which excess of the fecal sample can be scraped into the toilet bowl B.

OPERATION

The fecal collector 16 will be packaged in the mailer envelope 12 and a sheet of directions can be included therein. However, the unit will be such so that the relatively simple directions are printed thereon and this, in conjunction with the distributor's oral instructions, will generally be sufficient. The toilet seat T will be raised off the toilet bowl B, the lid L having been previously raised. After removing the fecal collector 16 from the envelope; it being understood that the kit will have been suitably sterilized, and the preaddressed envelope will not only serve as a packager, but also as the mailer. The collector is unfolded as seen in FIG. 2, and the pleated arrangement forms a slightly forward lowermost bag portion 58 depending below the rearward edge 54 of the bag-like portion. The tab 30 is disposed beneath the toilet seat T and the bag-like collector portion will be properly oriented beneath the users rectum. The forward edge 34 is sufficiently toward the rear to permit both male and female users to urinate without contaminating the fecal sample being collected. After the fecal deposit, the user can use the scraper 14 to scrape out excessive sample, and the user, after raising the toilet seat T, can then remove the laminated protector 59 off the pressure-sensitive adhesive 60 which is positioned to be engaged when the collector is refolded as seen in FIG. 1, whereafter the collector 16, and the scraper 15, can be reinserted into the mailer envelope 12 which, although biodegradable, is sufficiently impervious to permit mailing without exposure of the sample. The envelope may include on its flap 62 a pressure-sensitive adhesive 64 which is protected, until used, by a laminated cover 66.

Thus, there has been disclosed an exemplary embodiment of the invention which fully conforms with the object of the invention heretofore set forth. Various positional directional terms are used by way of example only and not by way of limitation.

What is claimed is:

1. A specimen collector for use in association with a toilet bowl comprising:
    a flat base element of size and shape as to effectively overlie the rear portion of the toilet bowl when in a normal operative position thereon for receiving the whole specimen discharged into the toilet bowl opening;
    said base element including a linear forward margin for defining a substantial forward opening with the toilet bowl and to permit ready urinal discharge into the toilet bowl without intermixing with the specimen being discharged;
    said base element including a rear portion for engagement beneath a toilet seat on the toilet seat for stabilizing the collector when a specimen is being discharged therein;
    said base element including a central portion defining a central through opening of sufficient diameter to be positioned beneath the rectum of one discharging the specimen;
    a collection bag secured to said base element and depending beneath and completely underlying the central through opening for catching the specimen being discharged; and
    said collection bag including a free rear margin disposed beneath the under-surface of said base element for permitting specimen-excess to be scraped therethrough and discharged into the toilet bowl.

2. The structure as claimed in claim 1, in which said collection bag comprises a foldable material, said base element including a fold-line extending through said linear margin and the rear portion of the element for defining two foldable and juxtapositional halves for being folded during both before and after a specimen is collected.

3. The structure claimed in claim 1, in which the entire collector comprises a biodegradable material.

4. The structure as claimed in claim 1, in which said collection bag comprises a paper-product material having micro-porosity for permitting residual moisture in the specimen to permeate therethrough and into the toilet bowl.

5. The structure as claimed in claim 1, in which said collection bag is adhesively secured to said base element.

6. The structure as claimed in claim 5, in which said collection bag includes a plurality of forward pleats overlying said base element for contouring the forward portion of said collection bag and reinforcing the same, said collection bag projecting through said central through opening and including a rear reinforced portion secured at opposite ends to the undersurface of said base element and forming the rear free edge margin of said collection bag.

7. The structure as claimed in claim 6, in which said rear reinforced portion of said collection bag comprises a marginal reverse fold at said free rear margin.

8. The structure as claimed in claim 2, in which said base element includes adhesive means on the upper surface thereof for securing said two juxtaposed halves in juxtaposed relation.

9. The structure as claimed in claim 8, in which said adhesive means comprises a pressure-sensitive adhesive covered by a removable protective laminate for exposing the adhesive in an operative condition and position when the halves are juxtaposed.

10. The structure as claimed in claim 2, in combination with a mailer envelope having a sealable closure for packaging said specimen collector before use, said mailer envelope being of a material to protect the integrity of the specimen being collected, said specimen collector and specimen being sealingly received in said mailer after collection.

11. In combination, a specimen collector for use in association with a toilet bowl, said specimen collector comprising:
    a flat base element of size and shape as to effectively overlie the rear portion of the toilet bowl when in a normal operative position thereon for receiving the whole specimen discharged into the toilet bowl opening;

said base element including a linear forward margin for defining a substantial forward opening with the toilet bowl and to permit ready urinal-discharge into the toilet bowl without intermixing with the specimen being discharged;

said base element including a rear portion for engagement beneath a toilet seat on the toilet seat for stabilizing the collector when a specimen is being discharged therein;

said base element including a central portion defining a central through opening of sufficient diameter to position beneath the rectum of one discharging the specimen;

a collection bag secured to said base element and depending beneath and completely underlying the central through opening for catching the specimen being discharged, said collection bag comprising a foldable material, said base element including a fold-line extending through said linear margin and the rear portion of the element for defining two foldable and juxtapositionable halves for being folded during both before and after a specimen is collected; and a mailer envelope having a sealable closure for packaging said specimen collector before use, said mailer envelope being of a material to protect the integrity of the specimen being collected, said specimen collector being sealingly received in said mailer envelope after collection.

* * * * *